United States Patent [19]

Hodam, Jr.

[11] Patent Number: 5,326,492

[45] Date of Patent: Jul. 5, 1994

[54] DISINFECTANT MIXTURE CONTAINING WATER SOLUBLE LUBRICATING AND CLEANING AGENTS AND METHOD

[75] Inventor: Robert H. Hodam, Jr., Sacramento, Calif.

[73] Assignee: Medical Polymers, Inc., Austin, Tex.

[21] Appl. No.: 793,596

[22] Filed: Nov. 18, 1991

[51] Int. Cl.$^5$ .................... C11D 3/48; A01N 25/34; A01N 35/02

[52] U.S. Cl. .............................. 252/106; 252/174.21; 252/174.23; 252/174.15; 252/547; 252/DIG. 2; 424/405; 514/694; 514/703; 514/693; 514/731; 514/724

[58] Field of Search ............. 252/106, 174.21, 174.23, 252/DIG. 2, 547, 174.15; 424/405; 514/694, 705, 693, 731, 724

[56] References Cited

U.S. PATENT DOCUMENTS

| | | | |
|---|---|---|---|
| 4,173,653 | 11/1979 | Law | 424/333 |
| 4,389,320 | 6/1983 | Clampitt | 252/8.551 |
| 4,632,772 | 12/1986 | Garabedian et al. | 252/106 |
| 4,753,844 | 6/1988 | Jones et al. | 428/296 |
| 4,804,685 | 2/1989 | Jacobs | 514/705 |

*Primary Examiner*—Anthony McFarland
*Assistant Examiner*—Nhat D. Phan
*Attorney, Agent, or Firm*—Winstead Sechrest & Minick

[57] ABSTRACT

Disinfectant mixture containing water soluble lubricating and cleaning agents comprising a water-based polymer serving as a water-based lubricant, a disinfectant and deionized water.

13 Claims, 2 Drawing Sheets

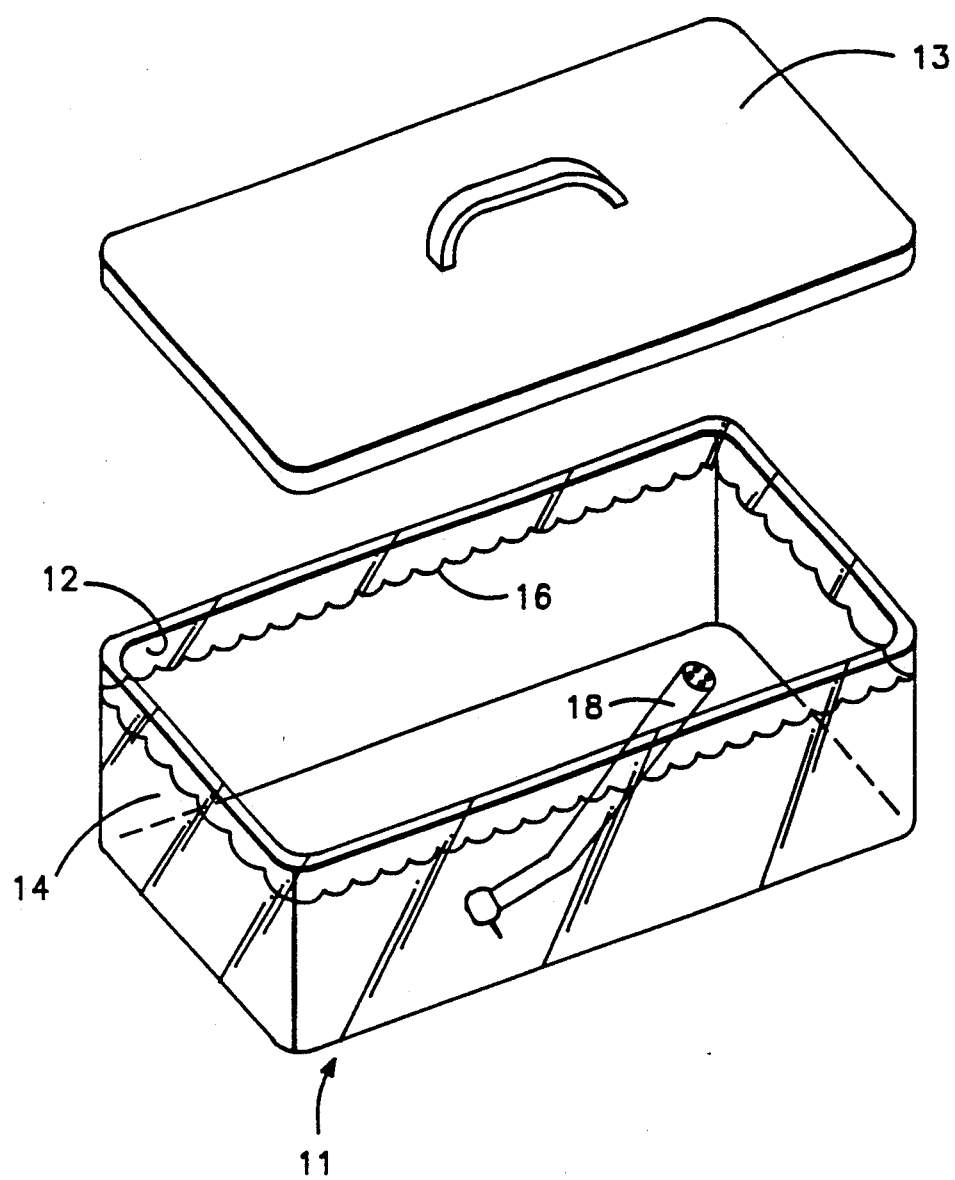
FIG.−1
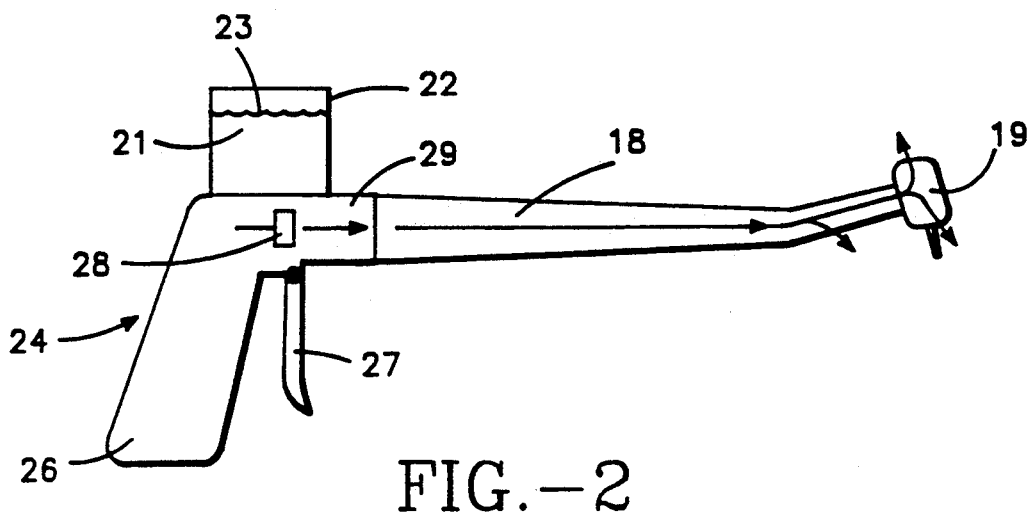
FIG.−2

DISINFECTANT MIXTURE CONTAINING WATER SOLUBLE LUBRICATING AND CLEANING AGENTS AND METHOD

TECHNICAL FIELD OF THE INVENTION

This invention relates to a disinfectant mixture containing water soluble lubricating and cleaning agents, and a method for use of the same, and more particularly to a disinfectant mixture for use with dental handpieces.

BACKGROUND OF THE INVENTION

Currently dental handpieces are cleaned once a week by soaking in alcohol, acetone or other disinfectants over the weekend. Typically there is no cleaning of the handpieces between patients. In addition, there is no disinfection between patients and there is no lubrication of the handpieces between patients. Currently it is impractical to lubricate dental handpieces between patients because typical lubricants used are oil based and have a tendency to cause bonding problems on the teeth because of oil which may come in contact with the enamel on the teeth. There is currently no practical method to disinfect dental handpieces between patients because chemical baths, chemclaves or autoclaves damage the dental handpieces. In addition, the chemclaves and autoclaves do not remove foreign material such as protein, organisms and blood from within the dental handpiece. Also, there is no current practice to clean the dental handpieces between patients. There is therefore a need for a disinfectant and a method to overcome these difficulties and to make it possible for the dental handpieces to be disinfected, lubricated and cleaned between patients.

SUMMARY OF THE INVENTION

In general, it is an object of the present invention to provide a disinfectant mixture which contains water soluble lubricating and cleaning agents and a method for utilizing the same for disinfecting dental handpieces.

Another object of the invention is to provide a mixture of the above character which makes it possible to perform disinfection, lubrication and cleansing in one step between patients.

Another object of the invention is to provide a mixture of the above character which is in liquid form and which can be readily used without dilution, mixing or other preparation.

Another object of the invention is to provide a mixture of the above character which has a relatively long shelf life.

Additional objects and features of the invention will appear from the following description in which the preferred embodiments are set forth in detail in conjunction with the accompanying drawings.

BRIEF DESCRIPTION OF THE DRAWING

FIG. 1 is an isometric view of a covered glass tray which can be utilized for receiving a quantity of the liquid disinfectant mixture of the present invention which can be utilized for treating dental handpieces immersed therein in accordance with the method of the present invention.

FIG. 2 is a side elevational view of a gun-like device which can be utilized for introducing the disinfectant mixture of the present invention into a dental handpiece to treat the same.

DETAILED DESCRIPTION OF THE INVENTION

Figure 3:
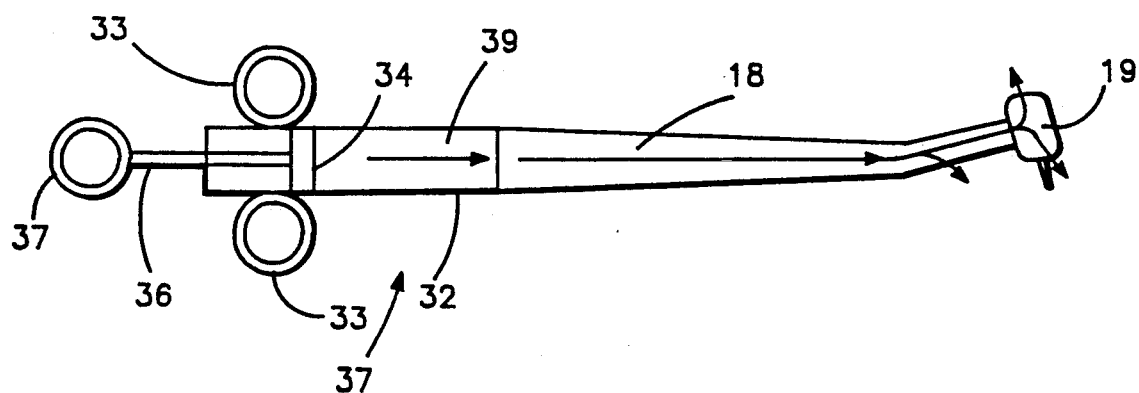
FIG. 3 is a side elevational view of a syringe which can be utilized for injecting a disinfectant mixture of the present invention into a dental handpiece to disinfect and sterilize the same.

In general, the disinfectant mixture comprises by weight 0.1 to 7.5 percent of a water-based polymer which serves as a water-based lubricant, and 1 to 10 percent by weight of a disinfectant, with the balance being deionized water. Also, 0.1 to 7.5 percent by weight of a surfactant, an anti-oxidant in the range of 0.25 to 1 percent and a dispersant in the range of 1 to 10 percent by weight can be utilized.

More in particular, the disinfectant mixture of the present invention contains water-soluble lubricating and cleaning agents and is comprised of a water-based polymer which is used for lubrication and include polyethylene oxide, polyacrylamides, polyethylene glycol and water soluble silicones or fluoro compounds (liquid "Teflon") which can be used singly or in combination. The mixture also is comprised of a broad range of disinfectants which contain antimicrobial chemicals and which are mixable with the water-soluble polymer to form an aqueous solution for the purpose of disinfection and lubrication. Disinfectants commonly available which can be used with water-based lubricants include phenols, alcohols, formaldehyde, glutaraldehyde, chlorohexidine, isophors and betadines. One or more of these disinfectants can be utilized with a water-based polymer or a combination of water-based polymers to which, if desired, a surfactant can be added. Suitable surfactants which may also act as disinfectants are quaternary ammonium chlorides and/or nonoxynol-9.

In general, the formulation can be comprised of 0.1 to 7.5 percent of a water-based polymer, 1 to 10 percent of the disinfectant, with the balance being deionized water. If a surfactant is used, it can be added in the range of 0.1 to 7.5 percent by weight of the total formulation. If desired, an anti-oxidant such as methyl paraben or propyl paraben can be added in the range of 0.25 to 1 percent by weight of the total formulation. A dispersant such as sorbitol, glycerine and ethanol in the range of 1 to 10% and preferably 3 to 8% by weight is used when polyethylene oxide is incorporated in the mixture.

EXAMPLE I

One specific formulation found to be particularly satisfactory is comprised of the following constituents in percentages by weight:

0.7% Polyox (polyethylene oxide)
5.0% Denatured Ethanol
4.0% Glutaraldehyde
Balance Deionized water When a surfactant is used in this specific formulation, it is introduced into the formulation in the following percentages by weight:

0.5% Quaternary ammonium chloride or
0.5% Nonoxynol-9

Alternatively, a mixture of the two can be used at the same percentage.

When an anti-oxidant is utilized, it is introduced into the formulation in the following percentages by weight:

0.5% Methyl paraben or propyl paraben

EXAMPLE II

Another formulation found to be particularly desirable had the following constituents in percentage by weight:
0.7% Polyethylene oxide at a 2,000,000 MW
4.0% Glutaraldehyde
1.0% Quaternary ammonium chloride
0.7% Nonoxynol-9
0.2% Methyl paraben
0.2% Propyl paraben
8.0% Glycerine
Balance Deionized water

EXAMPLE III

Another formulation is:
0.5% Polyacrylamide at a 4,000,000 MW
0.7% Quaternary ammonium chloride
4.0% Glutaraldehyde
0.5% Nonoxynol-9
Balance Deionized water Formulations using polyacrylamide do not require dispersants or anti-oxidants. Dispersants are not required because of the high solubility of polyacrylamide in water. Anti-oxidants are not required since polyacrylamide is very stable; however, they may be added to add to the corrosion resistance of the formulation.

In reviewing the formulations set forth above for the disinfectant mixture, the active ingredient for disinfection is glutaraldehyde. The surfactants, quaternary ammonium chloride and nonoxynol-9, both operate synergistically with glutaraldehyde to provide surface wetting. The two surfactants have different chemical structures and therefore provide different wetting characteristics for different kinds of proteins, and thus tend to provide a broad range of very high level surface wetting which should reach most proteins. These surfactants make the surfaces of the proteins wet to receive glutaraldehyde to make the glutaraldehyde more effective in a shorter period of time. It is believed that the surfactants provide openings in the protein in the organism, allowing the glutaraldehyde to penetrate that organism. These surfactants also act as lubricants to aid in lubrication. However, since they are surfactants their primary purpose is to emulsify proteins, blood, other foreign matter and saliva which become attached to the internal parts of dental handpieces.

It has been found that the disinfectant mixtures or solutions of the present invention are effective disinfectants at various pH values over the range of about 5 to 9. However, it has been observed that the greatest effectiveness occurs at approximately a pH of about 8.5. This pH is most readily achieved by titration with a base such as diluted sodium or potassium hydroxide or a tertiary amine such as triethanol amine. Conversely, it is possible to adjust the pH by the addition of disodium edetate or disodium acid phosphate or sodium borate. The anti-oxidant serves to reduce corrosion and to stabilize the polyox. The glycerine serves as a solvent dispersant and can range from 5% to 10% by weight. When polyacrylamide is used neither anti-oxidant nor dispersants are necessary.

The disinfectant mixture can be prepared by mixing the various liquid ingredients in a vat at room temperature and stirring the same. The mixture can then be packaged in suitable containers, as for example plastic or glass bottles, and shipped in cartons for use by the dentist.

Use of the disinfectant mixture by the dentist in a method in accordance with the present invention for treating dental handpieces may now be briefly described as follows.

The dentist or the dental assistant can take a container or bottle of the disinfectant mixture of the present invention and pour the liquid mixture into a tray 11, as shown in FIG. 1, formed of a suitable material such as autoclavable glass or stainless steel. The tray 11 can be of any suitable size and shape and, as shown, can be rectangular in form having an open top side 12. It can be of a suitable size such as 4 inches in width, 8 inches in length, and approximately 3 inches in depth. The tray 8 can be provided with a cover 13, as shown, which can be utilized for covering the top side opening 12. Let it be assumed that the liquid disinfectant mixture 14 has been poured into the tray 11 to the depth 16, as shown in FIG. 1.

The dental handpiece 18 to be treated in accordance with the present invention is disconnected from its compressed air line, placed in the liquid 14 in the tray 11, and allowed to remain therein at room temperature for a period of at least 10 minutes, permitting the liquid to penetrate into the water and air lines and into the head 19 of the dental handpiece 18. The dental handpiece 18 is then extracted from the liquid by suitable means such as by the use of tongs. It should be appreciated that although the human hand can be inserted into the liquid 14 to retrieve the handpiece, this is undesirable because of the need to maintain the cleanliness or purity of the liquid in the tray 11. The liquid disinfectant of the present invention is not dangerous to the human skin.

After the dental handpiece 18 has been retrieved from the liquid 16, it is permitted to drain onto a paper towel for a period of a few seconds. Any remaining liquid on the handpiece 18 can then be removed by a suitable manner, such as a paper towel or by cotton swabs. The dental handpiece 18 is then reconnected to its compressed air line. The air line is then turned on, blowing out the excess liquid from the air lines and the water lines and in the other parts of the dental handpiece, after which the dental handpiece can be placed in service for use with the next patient. This entire procedure should take less than approximately 5 minutes in the dentist's office.

Another alternative method for treating a handpiece is shown in FIG. 2 in which the liquid 21 is placed in a reservoir 22 to a level 23. The reservoir 22 is mounted on a gun 25 which is provided with a handle 26 adapted to be engaged by the palm of the hand, and a trigger lever 27 adapted to be engaged by the fingers of the same hand. The pivotally mounted trigger lever 27, by a mechanism well known to those skilled in the art, is utilized to advance a piston 28 to supply liquid from the reservoir into the barrel 29 of the gun 24.

The dental handpiece to be treated is removed from its compressed air line and is connected to the barrel 29 in a similar manner. The gun 24 is then operated to force the liquid by the use of the piston 28 from the reservoir 22 into and through the air lines and water lines in the handpiece, and out the head 19 of the handpiece. The liquid under pressure, in moving through the handpiece, serves to disinfect and clean the handpiece while also lubricating the same. The liquid under pressure also serves to remove any blood, saliva and the like through the openings in the head. Thereafter, after a suitable period of time as for example 2 to 5 minutes, the handpiece 18 can be removed from the gun 24.

Alternatively, a syringe 31 can be utilized for the same purpose, as shown in FIG. 3. The syringe 31 is provided with a barrel 32 which is provided with a pair of finger rings 33 on opposite sides of the same. A piston 34 is slidably mounted in the barrel and is mounted on the plunger 36 which carries another finger ring 37. The liquid disinfectant 39 is disposed within the barrel 32. The dental handpiece to be treated in accordance with the present method is disconnected from its compressed air line and is connected to the barrel 32 of the syringe 31. By two fingers of the hand engaging the finger rings 36 and the palm of the hand engaging the finger ring 37, liquid 39 under pressure can be forced out of the barrel into the air and water lines of the dental handpiece 18 and through the head 19 to disinfect, clean and lubricate the dental handpiece 18 in the manner hereinbefore described.

With the devices shown in FIGS. 2 and 3, if desired, the dental handpieces 18 could be permitted to soak in the liquid disinfectant by first forcing the liquid through the dental handpiece until it appears at the head. The dental handpiece could then be permitted to soak for a period of 2 to 5 minutes, after which the gun 24 or the syringe 31 can be utilized to force additional disinfectant into the dental handpiece to further clean, disinfect and lubricate the dental handpiece.

Figure 4:
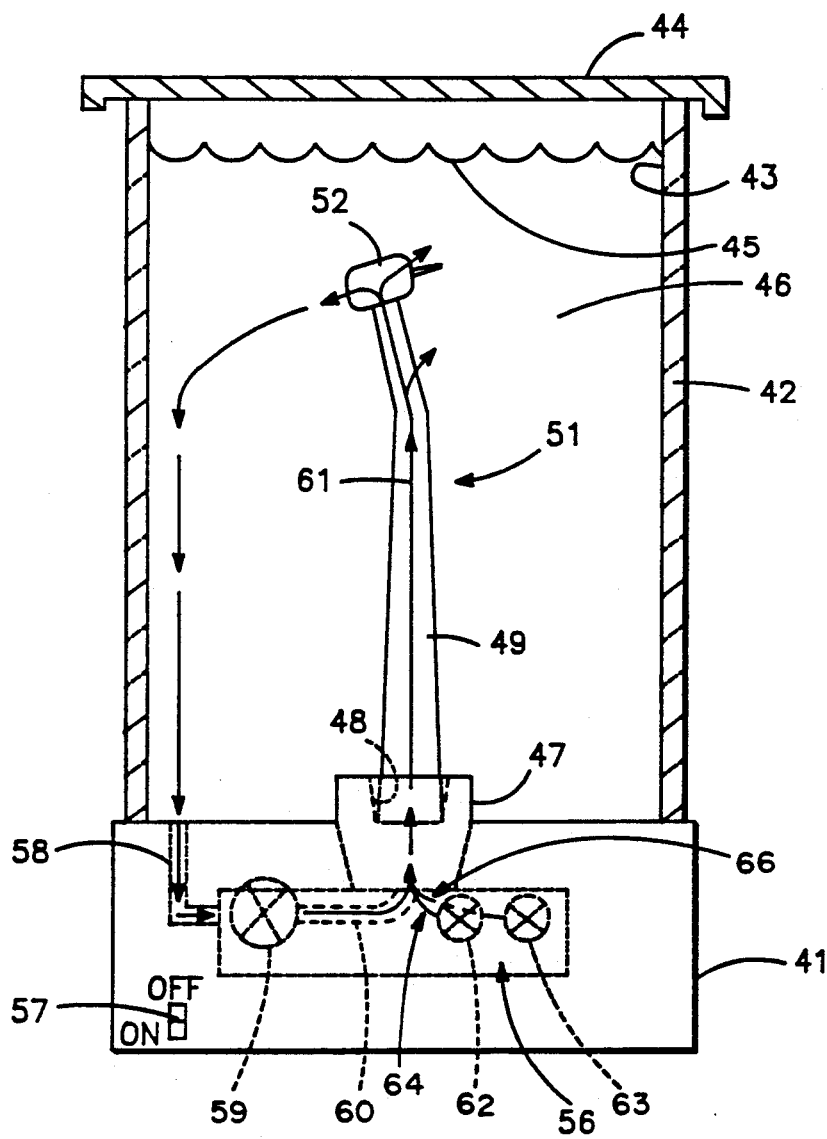
FIG. 4 is a side elevational view of a recirculation pump device containing a disinfectant mixture of the present invention which can be used for treating dental handpieces.

Another alternative device for utilizing the disinfectant mixture of the present invention for treating dental handpieces is shown in FIG. 4. The apparatus 41 as shown therein consists of a cylindrical base 41 formed of a suitable material such as stainless steel. A cylindrical vessel 42 formed of a suitable material such as glass is mounted thereon to provide a liquid tight seal. The vessel is provided with an open end 43 which is adapted to be closed by a lid 44. A liquid disinfectant mixture 46 of the present invention is provided in the interior of the vessel 42 to a level 45. A dental handpiece mounting 47 is mounted upon the base 41 within the vessel 42. The mounting 47 is provided with a tapered recess 48 which is adapted to receive the handle 49 of a conventional dental handpiece 51 having a head 52.

A recirculating pump assembly 56 is mounted within the base and is adapted to be connected to a suitable source of electric power through an on/off switch 57. The recirculating pump 56 is provided with an inlet 58 which opens into the interior of the vessel 42 to withdraw the disinfectant mixture therefrom and to pass through a pump 59 to reintroduce it into the vessel 42 through an outlet 60 to cause the disinfectant mixture to pass through the handpiece as indicated by the arrows 61. In addition, water and air lines 62 and 63 indicated schematically can be provided in the base 41 to supply air and/or water to the handpiece 51 and indicated by the arrows 64 and 66.

In the use of the apparatus shown in FIG. 4, the dentist or his assistant fills the vessel 42 with the disinfectant mixture to the level 45, then places the dental handpiece 51 to be treated into the vessel with the handle being fitted into the tapered recess 48. The pump 56 can then be turned on by operation of the switch 57 to cause the liquid disinfectant mixture to be forced through the dental handpiece as shown by the introduction of the liquid disinfectant into the handpiece 51. The dental handpiece 51 can be subjected to this recirculated disinfectant for a suitable period of time, as for example 2 to 5 minutes. If desired, air can be introduced into the handpiece 51 to form bubbles in the disinfectant as the disinfectant emerges from the handpiece to provide a visual effect. Thereafter, the dental handpiece can be removed from the apparatus shown in FIG. 4 and reconnected to air and water lines to remove any remaining disinfectant from the dental handpiece, permitting the dental handpiece to be used on the next patient.

It is readily apparent that the use of the gun 24 or the syringe 34 is particularly useful in treating the dental handpiece between patients.

When a tray is used for containing the liquid, as shown particularly in FIG. 1, it is believed that disinfectant will be effective for at least one week, so that on each Monday morning, at the first of the week, the dentist or the dental assistant can take a clean tray and fill the same with the disinfectant and cover the same with the cover 13 so that it is ready for use. The disinfectant is supplied so that it need not be diluted. It can be poured into the tray to the desired level and used for the entire week. At the end of the week, as for example on Friday, after the dentist has ceased work for the week, the disinfectant contained in the tray can be disposed of and the tray cleaned and dried for use on the following Monday.

The disinfectant of the present invention is particularly efficacious for disinfecting dental handpieces to prevent the transmission of disease from one patient to the other. The disinfectant mixture of the present invention is effective for killing HIV, TB, hepatitis B and polio. In particular, it has been found to be effective on HIV in less than 15 seconds, and no more than 10 minutes on the other organisms. The disinfectant mixture also has other advantages in that it cleans out blood and saliva from inside and outside dental handpieces when used between patients. Oil-free lubrication is provided which eliminates bonding problems encountered with previous lubricants. The disinfectant mixture is also non-corrosive. It does not have a strong smell or taste, and is non-toxic. Its use is advantageous because it provides extended handpiece life. It also makes possible lower operating costs for the dentist. The need for expensive oil lubricants is eliminated, which is particularly desirable because the removal of oil lubricants from dental handpieces in the past has required the use of strong solvents to clean out carbon build-up and organic matter. The water-based lubricants utilized in the disinfectant mixture of the present invention are water-soluble and can be washed out with warm water.

It is apparent from the foregoing that there has been provided a disinfectant for dental handpieces which, because of its inclusion of water-based lubricants, in addition to disinfecting and cleaning the dental handpiece will also lubricate the handpieces and is suitable with high-speed and low-speed dental handpieces. By providing a surfactant with the disinfectant, the formulation of the disinfectant mixture is particularly efficacious because of the synergistic effects of the surfactants in preparing the surface of protein for penetration by the glutaraldehyde.

What is claimed is:

1. A liquid disinfectant mixture consisting essentially of:
  from about 0.1 to about 7.5 weight percent, based on total weight of the composition, of a water-based polymer serving as a water-based lubricant, wherein said polymer is selected from the group consisting of polyethylene oxide, polyacrylamides, water soluble liquid silicone compounds and water soluble fluoridated compounds;

from about 1.0 to about 10 weight percent, based on total weight of the composition, of a disinfectant wherein said disinfectant is selected from the group consisting of phenols, alcohols, formaldehyde, glutaraldehyde, chlorehexidine, isophors and providone-iodine; and water.

2. A disinfectant mixture consisting essentially of:

about 0.7 weight percent, based on total weight of the composition, of polyethylene oxide;

about 4.0 weight percent, based on total weight of the composition, of glutaraldehyde; and water.

3. A disinfectant mixture consisting essentially of:

about 0.5 weight percent, based on total weight of the composition, of polyacrylamide;

about 4.0 weight percent, based on total weight of the composition, of glutaraldehyde; and water.

4. A liquid disinfectant mixture consisting essentially of:

from about 0.1 to about 7.5 weight percent, based on total weight of the composition, of a water-based polymer serving as a water-based lubricant, wherein said polymer is selected from the group consisting of polyethylene oxide, polyacrylamides, water soluble liquid silicone compounds and water soluble fluoridated compounds;

from about 0.1 to about 7.5 weight percent, based on total weight of the composition, of a surfactant;

from about 1.0 to about 10 weight percent, based on total weight of the composition, of a disinfectant wherein said disinfectant is selected from the group consisting of phenols, alcohols, formaldehyde, glutaraldehyde, chlorohexidine, isophors, and providone-iodine; and water.

5. A mixture as in claim 4 wherein said surfactant is selected from the group of quaternary ammonium chlorides and nonoxynol-9.

6. A liquid disinfectant mixture consisting essentially of:

from about 0.1 to about 7.5 weight percent, based on total weight of the composition, of a water-based polymer serving as a water-based lubricant, wherein said polymer is selected from the group consisting of polyethylene oxide, polyacrylamides, water soluble liquid silicone compounds and water soluble fluoridated compounds;

from about 0.25 to about 1.0 weight percent, based on total weight of the composition, of an anti-oxidant;

from about 0.1 to about 7.5 weight percent, based on total weight of the composition, of a surfactant;

from about 1.0 to about 10 weight percent, based on total weight of the composition, of a disinfectant wherein said disinfectant is selected from the group consisting of phenols, alcohols, formaldehyde, glutaraldehyde, chlorohexidine, isophors, and providone-iodine; and water.

7. A mixture as in claim 6 wherein said anti-oxidant is selected from the group of methyl parabens and propyl parabens.

8. A liquid disinfectant mixture consisting essentially of:

from about 0.1 to about 7.5 weight percent, based on total weight of the composition, of a water-based polymer serving as a water-based lubricant, wherein said polymer is selected from the group consisting of polyethylene oxide, and polyacrylamides;

from about 5 to about 10 weight percent, based on total weight of the composition, of a dispersant;

from about 1.0 to about 10 weight percent, based on total weight of the composition, of a disinfectant wherein said disinfectant is selected from the group consisting of phenols, alcohols, formaldehyde, glutaraldehyde, chlorohexidine, isophors, and providone-iodine; and water.

9. A mixture as in claim 8 wherein said dispersant is glycerine.

10. A disinfectant mixture consisting essentially of:

about 0.7 weight percent, based on total weight of the composition, of polyethylene oxide;

from about 0.5 to about 0.7 weight percent, based on total weight of the composition, of a surfactant;

about 4.0 weight percent, based on total weight of the composition, of glutaraldehyde; and water.

11. A disinfectant mixture consisting essentially of:

about 0.7 weight percent, based on total weight of the composition, of polyethylene oxide;

from about 5 to about 8 weight percent, based on total weight of the composition, of a dispersant;

about 4.0 weight percent, based on total weight of the composition, of glutaraldehyde; and water.

12. A disinfectant mixture consisting essentially of:

about 0.7 weight percent, based on total weight of the composition, of polyethylene oxide;

from about 0.2 to about 0.5 weight percent, based on total weight of the composition, of at least one anti-oxidant;

about 4.0 weight percent, based on total weight of the composition, of glutaraldehyde; and water.

13. A disinfectant mixture consisting essentially of:

about 0.5 weight percent, based on total weight of the composition, of polyacrylamide;

about 4.0 weight percent, based on total weight of the composition, of glutaraldehyde;

from about 0.5 to about 0.7 weight percent, based on total weight of the composition, of a surfactant; and water.

* * * * *